United States Patent
Fourcassie et al.

(10) Patent No.: US 10,307,445 B2
(45) Date of Patent: Jun. 4, 2019

(54) BACTERIAL STRAINS HAVING AN OUTSTANDING ABILITY TO PRODUCE MENAQUINONE

(71) Applicant: DUPONT NUTRITION BIOSCIENCES APS, Copenhagen K (DK)

(72) Inventors: Pascal Fourcassie, Poitiers (FR); Patrick Boyaval, Les Meziere (FR); Philippe Horvath, St-gervais-les-trois-clochers (FR)

(73) Assignee: DuPont Nutrition Bioscience ApS (DK)

( * ) Notice: Subject to any disclaimer, the term of this patent is extended or adjusted under 35 U.S.C. 154(b) by 0 days.

(21) Appl. No.: 14/860,071

(22) Filed: Sep. 21, 2015

(65) Prior Publication Data

US 2016/0008411 A1   Jan. 14, 2016

Related U.S. Application Data

(62) Division of application No. 13/259,894, filed as application No. PCT/EP2010/055002 on Apr. 15, 2010, now abandoned.

(60) Provisional application No. 61/169,494, filed on Apr. 15, 2009.

(51) Int. Cl.

| | |
|---|---|
| *C12N 1/20* | (2006.01) |
| *C12P 7/66* | (2006.01) |
| *A61K 35/74* | (2015.01) |
| *A23C 9/123* | (2006.01) |
| *A23C 19/032* | (2006.01) |
| *C12R 1/01* | (2006.01) |
| *C12R 1/46* | (2006.01) |
| *A23K 10/18* | (2016.01) |
| *A23L 33/135* | (2016.01) |
| *A61K 35/744* | (2015.01) |
| *A23L 33/15* | (2016.01) |

(52) U.S. Cl.
CPC ............ *A61K 35/74* (2013.01); *A23C 9/1234* (2013.01); *A23C 9/1236* (2013.01); *A23C 19/0323* (2013.01); *A23K 10/18* (2016.05); *A23L 33/135* (2016.08); *A23L 33/15* (2016.08); *A61K 35/744* (2013.01); *C12N 1/20* (2013.01); *C12P 7/66* (2013.01); *C12R 1/01* (2013.01); *C12R 1/46* (2013.01); *A23V 2002/00* (2013.01); *A23Y 2240/21* (2013.01); *A23Y 2240/41* (2013.01); *A23Y 2320/39* (2013.01)

(58) Field of Classification Search
None
See application file for complete search history.

(56) References Cited

U.S. PATENT DOCUMENTS

| | | |
|---|---|---|
| 7,981,657 B2 | 7/2011 | Garault et al. |
| 8,361,525 B2 | 1/2013 | Garault et al. |

FOREIGN PATENT DOCUMENTS

| | | |
|---|---|---|
| EP | 1230920 A1 | 8/2002 |
| WO | 2008/040784 A1 | 4/2008 |
| WO | 2008/040793 A1 | 4/2008 |
| WO | 2009/095240 A1 | 8/2009 |

OTHER PUBLICATIONS

Furuichi et al., "Aerobic Culture of Propionibacterium Freudenreichii ET-3 Can Increase Production Ratio of 1,4-dihydroxy-2-naphthoic acid to menaquinone", J. Biosci. Bioeng., 101(6)464-470 (2006) XP025182913.

Morishita et al., "Production of Menaquinones by Lactic Acid Bacteria", J. Dairy Sci., 82(9):1897-1903 (1999) XP026993651.

Rezaiki et al., "Lactococcus lactis produces short-chain quinones that cross-feed Group B *Streptococcus* to activate respiration growth", Molecular Microbiology (2008) 67(5), 947-957.

Sato et al., "Efficient production of menaquinone (vitamin K2) by a menadione-resistant mutant of Bacillus subtilis", J. Industrial Microbio. Biotechnol., 26(3)115-120 (2001) XP002241832.

Survase Shrikant et al., "Biotechnological production of vitamins", Food Technol. Biotechnol., 44(3):381-396 (2006) XP008123838.

International Search Report and Written Opinion for PCT/EP2010/055002, dated Jul. 6, 2010.

*Primary Examiner* — Irene Marx

(57) ABSTRACT

The invention relates to bacterial strains having an outstanding ability to produce menaquinone and to applications thereof.

20 Claims, No Drawings

BACTERIAL STRAINS HAVING AN OUTSTANDING ABILITY TO PRODUCE MENAQUINONE

The present application is a divisional of U.S. patent application Ser. No. 13/259,894, which was filed Sep. 23, 2011, which was filed pursuant to 35 U.S.C. 371 as a U.S. National Phase application of International Patent Application No. PCT/EP2010/055002, which was filed Apr. 15, 2010, claiming the benefit of priority to U.S. Provisional Patent Application No. 61/169,494, which was filed on Apr. 15, 2009. The entire text of the aforementioned applications is incorporated herein by reference in its entirety.

FIELD OF THE INVENTION

The invention relates to bacterial strains having an outstanding ability to produce menaquinone.

BACKGROUND OF THE INVENTION

Menaquinone or vitamin K2 is involved in the carboxylation of certain glutamate residues in proteins to form gamma-carboxyglutamate residues (abbreviated Gla-residues). The modified residues are often (but not always) situated within specific protein domains called Gla domains. Gla-residues are usually involved in binding calcium. The Gla-residues are essential for the biological activity of all known Gla-proteins (Furie B, Bouchard B A, Furie B C; Blood 93 (6): 1798-808). To date, 14 human proteins with Gla domains have been discovered, and they play key roles in the regulation of three physiological processes, such as blood coagulation (prothrombin (factor II), factors VII, IX, X, protein C, protein S and protein Z); bone metabolism (osteocalcin, also called bone Gla-protein (BGP), and matrix gla protein (MGP); and vascular biology.

Accordingly, menaquinone deficiency may induce several pathologies such as for example bleeding, coagulation dysfunctions, osteoporosis . . . . Typically, the groups of patients which are considered to be particularly exposed to a menaquinone deficiency are the new born, the elderly, the patients having liver, bile or intestinal dysfunctions, and patients having chronic antibiotic treatment.

Several methods have been proposed in the prior art to supplement the menaquinone deficiency of these patients. One of these methods consists to administer to these patients menaquinone-producing bacteria. Indeed, menaquinone is produced by the bacteria of the intestinal flora, and in particular by the bacteria of the species *Escherichia coli*, *Bacillus subtilis* and *Bacteroides* subsp. Menaquinone is also produced by several lactic acid bacteria, such as for example the bacteria of the genera *Bifidobacterium, Lactococcus, Leuconostoc, Enteroccocus* and *Propionibacterium*. In particular, a specific variant of *Lactococcus lactis* subsp. *cremoris* having the ability to produce more menaquinone than the corresponding wild type strain has been recently disclosed in WO 2008/040793.

However, having strains capable of producing higher amounts of menaquinone would be very interesting.

SUMMARY OF THE INVENTION

The invention relates to bacterial strains having an outstanding ability to produce menaquinone. Indeed, during their research, the inventors have found that the particular strains according to the invention present an exceptional ability to produce menaquinone compared to the other strains known to date. These strains have been deposited under the Budapest Treaty under the following accession numbers: CNCM I-4128, DSM 23476, DSM 23477, DSM 23478, DSM 23479.

The invention particularly relates to the use of these strains and variants thereof for producing menaquinone.

DETAILED DESCRIPTION OF THE INVENTION

The invention relates to bacterial strains having an outstanding ability to produce menaquinone as compared to other strains known to date.

An object of the invention concerns a strain of *Lactococcus lactis* subsp. *cremoris* deposited by Danisco France SAS (20, rue de Brunel, 75017 Paris, France) under the Budapest Treaty on 24 Feb. 2009 at the Collection Nationale de Cultures de Microorganismes (CNCM, Institut Pasteur, 25, rue du Docteur Roux, 75724 Paris cedex 15, France) under number CNCM I-4128, or a variant thereof. The strain CNCM I-4128 or variants thereof produce high quantities of menaquinone. In particular, the inventors have shown that the strain CNCM I-4128 produce at least 7 µg of menaquinone per 100 g of milk fermented with said strains when measured in a Test A.

Typically, the variants of the strain CNCM I-4128 produce at least 7 µg, particularly at least 8 µg, still particularly at least 9 µg, more particularly at least 10 µg, still more particularly at least 11 µg and most particularly at least 12 µg of menaquinone per 100 g of milk fermented with said variant when measured in a Test A according to the invention.

Test A is fully described in the experimental section. Briefly, Test A comprises the following steps:
  inoculating two flasks comprising 100 mL of skimmed UHT milk, with $5.10^4$ to $10^7$ cfu/mL of the strain to be tested,
  incubating the inoculated flasks without stirring at a constant temperature selected in the range from 23° C. to 30° C. in a water bath,
  measuring and recording the evolution of the pH in one of the two flasks with a pH probe of a Cinac System (Ysebaert system),
  stopping the incubation when the pH reaches 4.60+/−0.1 by cooling down to 6° C. the flask wherein the pH has not been measured,
  storing said flask at 6° C. during 14 h to 20 h,
  homogenizing the milk manually,
  performing a chemical extraction of menaquinone and measuring the quantity of menaquinone following the protocol P.

In another embodiment of the invention, the variants of the strain CNCM I-4128 produce at least 200 µg, particularly at least 230 µg, more particularly at least 260 µg of menaquinone per 100 g of freeze-dried cells when measured in a Test B.

Test B is fully described in the experimental section. Briefly, Test B comprises the following steps:
  culturing $1.10^2$ to $1.10^7$ cfu/ml of the strain to be tested during 14 h to 20 h in 50 ml of M17-lactose broth medium (Biokar BK088HA) at 30° C.,
  centrifuging 25 mL of the culture at 8000 rpm during 10 minutes,
  discarding the supernatant and resuspending the pellet with 25 mL of a tryptone salt solution (0.1% tryptone, 0.85% salt), centrifuging the resuspended culture at 8000 rpm during 10 minutes, discarding the supernatant and resuspending the pellet in 25 ml of reconstituted milk powder at 10% (w/w), placing the cell suspension in a freeze dryer, obtaining between 2 and 4 grams of freeze-dried cells, performing the chemical extraction of menaquinone and measuring the quantity of menaquinone following the protocol P.

Protocol P is the Following:

A sample consisting of 10 ml of fermented milk (for test A) or 10 mL of a ten times dilution in ethanol/water (50/50 V/V) of freeze-dried cells (for test B) is mixed with 5 ml of HCl 1N. The sample is then heated at 100° C. during 10 min in a water bath. Then, 10 ml of isopranol are added in the tube. The tube is placed 10 min in a water bath at 22° C. (+/−3° C.) equipped with ultra sounds. 5 ml of hexane are added in the tube. The tube is mixed by vortexing during 5 min.

The suspension is centrifuged at 4600 rpm during 5 min. Then the organic phase is harvested and again centrifuged during 5 min at 4600 rpm. The organic phase is then harvested and concentrated with a speed vac system in order to obtain a dry product. The dry product is rehydrated with 1 ml ethanol and filtrate on 0.45 µm filter. This extract is injected in a HPLC system. Separation and detection of menaquinone are performed using methods described in Hojo K. et al., "Quantitative measurement of tetrahydromenaquinone-9 cheese fermented by propionibacteria", J. dairy Science, 2007, 90, 9. 4078-4083. The detection is performed by a fluorometer after post-column reduction of menaquinone by Zn. Vitamin K1 is used as internal standard for extraction/purification steps and MK-4 (Sigma V9378) is used as external calibration for quantification.

The invention also concerns a strain of *Lactococcus lactis* spp. *cremoris* deposited by Danisco Deutschland GmbH (Busch-Johannsen-Str. 1, 25899 Niebüll, Germany) under the Budapest Treaty on 24 Mar. 2010 at the Deutsche Sammlung von Mikroorganismen and Zellkulturen (DSMZ, Inhoffenstr. 7B, D-38124 Braunschweig, Germany) under number DSM 23476, or a variant thereof.

The strain DSM 23476 or variants thereof produce high quantities of menaquinone. The variants of the strain DSM 23476 typically produce at least 25 µg of menaquinone per g of freeze-dried cells when measured in a Test C according to the invention.

In one embodiment, the variants of the strain DSM 23476 typically produce at least 30 µg, particularly at least 35 µg, still particularly at least 40 µg, more particularly at least 45 µg, still more particularly at least 50 µg, again more particularly at least 55 µg, and most particularly at least 60 µg of menaquinone per g of freeze-dried cells when measured in a Test C according to the invention.

The invention also concerns a strain of *Lactococcus lactis* spp *lactis* deposited by Danisco Deutschland GmbH (Busch-Johannsen-Str. 1, 25899 Niebüll, Germany) under the Budapest Treaty on 24 Mar. 2010 at the Deutsche Sammlung von Mikroorganismen und Zellkulturen (DSMZ, Inhoffenstr. 7B, D-38124 Braunschweig, Germany) under number DSM 23477, or a variant thereof.

The strain DSM 23477 or variants thereof produce high quantities of menaquinone. The variants of the strain DSM 23477 typically produce at least 15 µg of menaquinone per g of freeze-dried cells when measured in a Test C according to the invention.

In one embodiment, the variants of the strain DSM 23477 typically produce at least 20 µg, particularly at least 25 µg, still particularly at least 30 µg, more particularly at least 35 µg, still particularly at least 40 µg of menaquinone per g of freeze-dried cells when measured in a Test C according to the invention.

The invention also concerns a strain of *Lactoccus lactis* spp *cremoris* deposited by Danisco Deutschland GmbH (Busch-Johannsen-Str. 1, 25899 Niebüll, Germany) under the Budapest Treaty on 24 Mar. 2010 at the Deutsche Sammlung von Mikroorganismen und Zellkulturen (DSMZ, Inhoffenstr. 7B, D-38124 Braunschweig, Germany) under number DSM 23478, or a variant thereof.

The strain DSM 23478 or variants thereof produce high quantities of menaquinone. The variants of the strain DSM 23478 typically produce at least 30 µg of menaquinone per g of freeze-dried cells when measured in a Test C according to the invention.

In one embodiment, the variants of the strain DSM 23478 typically produce at least 35 µg, particularly at least 40 µg, still particularly at least 45 µg, more particularly at least 50 µg, still more particularly at least 55 µg of menaquinone per g of freeze-dried cells when measured in a Test C according to the invention.

Briefly, Test C according to the invention comprises the following steps: 1) Culturing the strain: 1.A) the strain stored in a viable physiological state at temperature below −20° C. is first sub-cultured in a synthetic medium (Lactose 50 g/l, Yeast Extract powder 36 g/l, Mn SO$_4$H$_2$O 1 g/l, Mg SO$_4$7H$_2$O 1 g/l) at 30° C.+/−2° C. overnight, 1.B) from 2% to 5% (V/V) of the first culture obtained after step 1.A) is then sub-cultured in synthetic medium from 10 h to 24 h, at a temperature comprised between 25° C. and 35° C., a pH maintained in the range 5.0-7.5 by alkali addition, and dissolved oxygen kept below 2% during the entire step, 2) Concentrating the strain: the cultured strain obtained after step 1.B) is concentrated with a centrifuge separator until a concentration comprised between $2.10^{10}$ cfu/ml and $6.10^{11}$ cfu/ml is obtained; the concentrate thus obtained is then cooled at a temperature below 12° C.;

3) Preserving the strain: 30 to 70% (w/w) of skimmed milk powder is directly added to the concentrate, frozen at −55° C., pelletized to obtain frozen pellets, and freeze dried in a freeze drier to achieve a Aw with in the range 0.05-0.35 (measured with 3TE Aqualab Ltd device), 4) Extracting and measuring the quantity of menaquinone following the protocol Q according to the invention.

Protocol Q Comprises the Following Steps:

1) Extracting menaquinone (all the steps of the extraction are carried out in subdued light to prevent the deterioration of K vitamins):

Put 10 mL of a solution containing 0.5 g of freeze dried material in 100 mL of nanopure water in a 50 mL amber Falcon tube (Ø30×115 mm-Ref 525-0397 VWR), Add 100 µL of internal standard (Vitamin K1 at 20 µg/mL in ethyl alcohol) and 5 mL of hydrochloric acid 1N, Put the tube in a 100° C. bath during 10 min, After cooling, add 10 mL of isopropanol, Sonicate the sample during 10 min, Add 5 mL of hexane, shake the sample for 5 min, Centrifuge 5 min at 3760 g and collect the organic layer (upper layer) in a 15 mL amber Falcon tube (Ø17×120 mm-Ref 525-0395 VWR), Repeat this step twice, After collecting the two organic layers, they are evaporated to dryness in a vacuum evaporator Speed-Vac (about 30 min), Dissolve the residue in 1 mL of ethanol, The sample is filtered through a Nylon 0.45 µm filter and placed in a HPLC vial, 2) measuring the quantity of menaquinone in the sample by HPLC.

HPLC Analysis:

High performance liquid chromatography coupled to a fluorimetry detector is used in order to analyse vitamin K. Different forms of vitamin K are separated on a reverse phase column and reduced through a post column. Identified and measured forms of vitamin K2:

$K_2$ vitamin (MK-n) MK-4
MK-5
MK-6
MK-7
MK-8
MK-9
MK-10

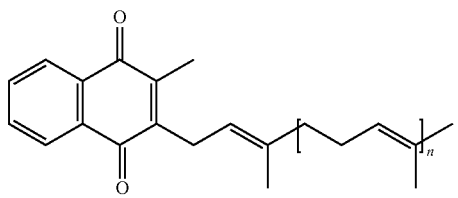

B $K_1$ vitamin used as internal standard

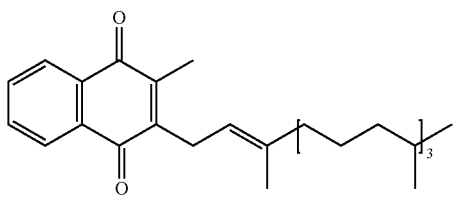

A

Products and Solutions:

K1 Vitamin, Sigma V3501-1G, CAS 84-80-0

K2 Vitamin, (MK-4), Sigma V9378-250MG, CAS 11032-49-8

Mobile Phase:

In a flask with 830 mL of methanol and 170 mL of ethanol, add 0.68 g of sodium acetate, 1.36 g of zinc chloride and 300 µL of acetic acid.

Shake the mix and sonicate it during 10 min.

The analysis is carried out by an Agilent HPLC 1100 in reverse phase with a fluorescence detector. In order to improve vitamin K's sensibility detection, it's reduced after separation in hydroquinone by chemical reduction with zinc metal. Hydroquinones are more fluorescent than quinones.

Reduction: Quinone+2 $e^-$+2$H^+$→$H_2Q$ (Hydroquinone) $E°$=+0.70V

Oxidation: Zn→$Zn^{2+}$+2 $e^-$ $E°$=−0.76V

Balance: Quinone+2$H^+$+Zn→$H_2Q$ (Hydroquinone)+$Zn^{2+}$

Analytical Conditions:

Column: Capcell Pak 5 µm SG-C18, 250×4.6 mm (Phenomenex)

Post column reduction: Reactor post column zinc, 20×4 mm.

Mobile phase:
83% of methanol
17% of ethanol
5 mM of sodium acetate
10 mM of $ZnCl_2$
5 mM of acetic acid Flow: 1 mL/min (isocratic elution)

Column temperature: 55° C.

Detector: $\lambda_{ex}$=220 nm, $\lambda_{em}$=436 nm

Injection volume: 10 µL

Menaquinone Quantification:

The internal standard, Vit K1, is used to calculated the yield of extraction/purification for each sample preparation. For calibration of the technique, a calibration curve has been obtained for K2 Vitamin, (MK-4), Sigma V9378-250MG. The response coefficient of MK-4 is applied for the other form of MK. It allows to transform peak surface area into Mk-4 equivalent concentration in the sample for each MK-form. Furthermore, for each form of MK's, the concentration in mass for each form is calculated taking into account the differences in molecular mass between menaquinone MK-4 and MK form considered. For example, the molecular mass of MK4 is 512 g/mol, the molecular mass of MK9 is 852 g/mol, therefore 1 µg of MK4 will give exactly the same peak surface area than 1.66 µg of MK9. This principle of calculation is used for each MK form.

The invention also concerns a strain of *Propionibacterium freudenreichii* subsp. *Shermanii* deposited by Danisco Deutschland GmbH (Busch-Johannsen-Str. 1, 25899 Niebüll, Germany) under the Budapest Treaty on 24 Mar. 2010 at the Deutsche Sammlung von Mikroorganismen and Zellkulturen (DSMZ, Inhoffenstr. 7B, D-38124 Braunschweig, Germany) under number DSM 23479, or a variant thereof.

The strain DSM 23479 or variants thereof produce high quantities of menaquinone. A variant of the strain DSM 23479 typically produces at least 15 µg of menaquinone per 100 g of milk fermented with said variant when measured in a Test D according to the invention.

In one embodiment, a variant of the strain DSM 23479 typically produces at least 15 µg, particularly at least 20 µg, still particularly at least 25 µg of menaquinone per 100 g of milk fermented with said variant when measured in a Test D according to the invention.

Test D according to the invention comprises the following steps:

inoculating two flasks comprising 100 mL of a skimmed UHT milk supplemented with 1.6 ml of pure D-L lactate and 0.2% of yeast extract powder and heat treated 20 minutes at 110° C., with $5.10^4$ to $10^7$ cfu/mL of the strain to be tested, incubating the inoculated flasks without stirring at a constant temperature selected in the range from 23° C. to 30° C. in a water bath, measuring and recording the evolution of the pH in one of the two flasks with a pH probe of a Cinac System (Ysebaert system), stopping the incubation when the pH reaches 4.60+/−0.1 by cooling down to 6° C. the flask wherein the pH has not been measured, storing said flask at 6° C. during 14 h to 20 h, homogenizing the milk manually, performing a chemical extraction of menaquinone and measuring the quantity of menaquinone following the protocol P according to the invention.

According to the invention, by "variant" it is meant:
- a natural variant of the strain according to the invention, i.e. a variant obtained spontaneously from the strain according to the invention after incubation in a selection medium. A natural variant is thus obtained without any genetic manipulation of the operator but only by natural mutation of the strain and selection of the strain in an appropriate medium, or
- a variant of the strain according to the invention comprising at least one mutation in their genome, said mutation being induced by genetic engineering, for instance by directed mutagenesis or random mutagenesis. For instance, random mutagenesis can be performed with UV radiations or mutagenic compounds such as nitrous acid, ethyl-methanesulfonate, N-Methyl-N'-nitro-N-nitrosoguanidine, N-ethyl-N-nitrosourea, acridine orange, proflavine.

By "mutation" according to the invention, it is meant the addition, deletion, or the substitution of at least one nucleotide in the genome of the strain according to the invention.

The strains according to the invention or variants thereof, are thus very interesting in term of health benefits, but also in term of marketing. For example, in Europe when a product contains at least 11.5 µg of menaquinone per serving size, more particularly per 100 g or per 100 mL of product, it can be labelled as "source of" vitamin K2.

Another object of the invention concerns the use of the strains or variants thereof according to the invention for producing menaquinone. An application of the invention is the use of the outstanding properties of the strains and variants thereof according to the invention to produce important amounts of menaquinone at an industrial scale. The menaquinone can then be extracted from the cultures of strains according to the invention and be used in all kinds of preparations, for instance in pharmaceutical preparations, feed and food preparations such as a dairy product, or dietary supplements.

The invention thus also concerns a method for producing menaquinone, comprising the step of culturing a strain or a variant thereof according the invention in a substrate. Said substrate can be selected from any appropriate substrate known by the skilled person. Examples of appropriate substrates are milk substrates, in particular selected from the group consisting of natural or reconstituted milk, skimmed or otherwise, milk-based media and media based on products of dairy origin.

Another object of the invention is a strain or a variant thereof according to the invention, for use in a method for treatment of the human or animal body.

Typically, the strains or variants thereof according to the invention are useful in the treatment of the diseases associated with a deficiency in menaquinone, as for instance bone, vascular and/or skin health diseases such as osteoporosis, cardiovascular diseases, blood pressure dysfunctions, blood clotting, loss of skin elasticity.

The invention thus relates to a method for treating a disease selected from the group comprising bone diseases such as osteoporosis; vascular diseases such as cardiovascular diseases, blood pressure dysfunctions and blood clotting; and skin diseases, such as loss of skin elasticity; said method comprising the step of administering to a patient in need thereof, a therapeutically effective amount of a strain or of a variant thereof according to the invention.

The invention also relates to a method for improving calcium fixation on the bones, maintaining or improving the bone structure and/or resistance, and/or improving the bone development, said method comprising the step of administering to a patient in need thereof, an effective amount of a strain or of a variant thereof according to the invention. Alternatively, the invention relates to the strains or variants thereof according to the invention, for use in a method for improving calcium fixation on the bones, maintaining or improving the bone structure and/or resistance, and/or improving the bone development.

The term "treating" or "treatment", as used herein, means reversing, alleviating, inhibiting the progress of, or preventing the disorder or condition to which such term applies.

As used herein, "patient" refers to a human or animal that may benefit from the administration of a strain or a variant thereof as recited herein.

By a "therapeutically effective amount" of a strain or a variant thereof as described previously, it is meant a sufficient amount to treat the disease, at a reasonable benefit/risk ratio applicable to any medical treatment.

In a particular embodiment of the method for treatment of the invention, the strain or a variant thereof can be used alive or under a specific preserved state. When the strain or variant thereof is used in a preserved state, the strain has been preferably previously cultured to enrich its content in menaquinone. By "preserved state" it is meant a strain that has been dried, freeze-dried or frozen for example. The strain or a variant thereof may also be used after having been inactivated, for instance by heat treatment, by chemical treatment and/or by other treatments known by the skilled person in the art.

Another aspect of the invention concerns the preparation of products enriched in menaquinone by using the strains or variants thereof according to the invention. These products are thus particularly useful for supplementing any deficiency in menaquinone occurring in a patient in need thereof. Such deficiency in menaquinone is for instance encountered in the newborn infants, individuals who suffer from liver damage or disease (i.e. alcoholics), people with cystic fibrosis, inflammatory bowel diseases or those who have recently had abdominal surgeries. Groups which may suffer from secondary vitamin K deficiency include bulimics, those on stringent diets and those taking anticoagulants.

Accordingly, the invention concerns the use of a strain or a variant thereof according to the invention for preparing a product. This product is typically selected from the group consisting of a dietary supplement, a pharmaceutical preparation, a food preparation and a feed preparation. In a particular embodiment, in these products, the strain or a variant thereof can be used alive or under a specific preserved state. When the strain or variant thereof is used in a preserved state, the strain has been preferably previously cultured to enrich its content in menaquinone. By "preserved state" it is meant a strain that has been dried, freeze-dried or frozen for example. The strain or a variant thereof may also be used after having been inactivated, for instance by heat treatment, by chemical treatment and/or by other treatments known by the skilled person in the art.

The invention also relates to a product typically selected from the group comprising of a dietary supplement, a pharmaceutical preparation, a food preparation and a feed preparation, wherein said product comprises a strain or a variant thereof according to the invention.

According to the invention, by "dietary supplement" it is meant a product or a composition that is intended to supplement the diet of the human or of an animal. A dietary supplement according to the invention is typically intended for ingestion in pill, capsule, tablet, or liquid form.

According to the invention, by "pharmaceutical preparation" it is meant a preparation that is intended to be used in a method for treatment of the human or animal body. In the context of the invention, the term "treatment", as used herein, means reversing, alleviating, inhibiting the progress of, or preventing a disorder or condition. Typically, the pharmaceutical preparation according to the invention comprises the strain or a variant thereof according to the invention together with a pharmaceutically acceptable carrier.

According to the invention, by "food preparation" it is meant a preparation that is intended to feed a human.

According to the invention, by "feed preparation" it is meant a preparation that is intended to feed an animal.

In a particular embodiment of the invention, said product is a food preparation. More particularly, the food preparation is a dairy product. Within the meaning of the invention, by "dairy product" it is meant fermented milk, a yogurt, a matured cream, a cheese, a fromage frais, a milk drink, a dairy product retentate, a processed cheese, a cream dessert, a cottage cheese or an infant milk. Still typically, the dairy product according to the invention comprises milk of animal and/or plant origin.

Another aspect of the invention concerns the application of the strains and variants thereof according to the invention to enrich the content of a product in menaquinone. Accordingly, the invention relates to a method for enriching the menaquinone content of a product selected from the group consisting of a dietary supplement, a pharmaceutical preparation, a food preparation and a feed preparation, comprising the step of adding to said product a strain or a variant thereof according to the invention. In a particular embodiment of this method, the strain or a variant thereof can be used alive or under a specific preserved state. When the strain or variant thereof according to the invention is used in a preserved state, the strain has been preferably previously cultured to enrich its content in menaquinone. By "preserved state" it is meant a strain that has been dried, freeze-dried or frozen for example. The strain or a variant thereof may also be used after having been inactivated, for instance by heat treatment, by chemical treatment and/or by other treatments known by the skilled person in the art.

The present invention is better illustrated below using the examples which follow. These examples are given only by way of illustration of the subject-matter of the invention, of which they in no way constitute a limitation.

EXAMPLES

Example 1: Measurement of the Production of Menaquinone by the Strain CNCM I-4128, Following TEST B The strain CNCM I-4128 has been compared to 23 other strains belonging to the *Lactococcus lactis* species for their production of menaquinone (following TEST B).

For each strain, the following protocol has been followed:
culturing $1.10^2$ to $1.10^7$ cfu/ml of the strain during 18 h in 50 ml of M17-lactose broth medium (Biokar BK088HA) at 30° C.,
centrifuging 25 mL of the culture at 8000 rpm during 10 minutes,
discarding the supernatant and resuspending the pellet with 25 mL of a tryptone salt solution (0.1% tryptone, 0.85% salt),
centrifuging the resuspended culture at 8000 rpm during 10 minutes,
discarding the supernatant and resuspending the pellet in 25 ml of reconstituted milk powder at 10% (w/w),
placing the cell suspension in a freeze dryer,
obtaining between 2 and 4 grams of freeze-dried cells.

The chemical extraction of menaquinone and the measurement of its quantity have been performed according to the following protocol:

The freeze-dried cells obtained in Test B are diluted ten times in ethanol/water (50/50 V/V). 10 mL of this dilution are mixed with 5 ml of HCl 1N. The sample is heated at 100° C. during 10 min in a water bath. Then, 10 ml of isopranol are added in the tube. The tube is placed 10 min in a water bath at 22° C. (+/−3° C.) equipped with ultra sound. 5 ml of hexane are added in the tube. The tube is mixed by vortexing during 5 min.

The suspension is centrifuged at 4600 rpm during 5 min. Then the organic phase is harvested and again centrifuged during 5 min at 4600 rpm. The organic phase is then harvested and concentrated with a speed vac system in order to obtain a dry product. The dry product is rehydrated with 1 ml ethanol and filtrate on 0.45 µm filter. This extract is injected in a HPLC system. Separation and detection of menaquinone are performed using methods described in Hojo K. et al., "Quantitative measurement of tetrahydromenaquinone-9 cheese fermented by propionibacteria", J. dairy Science, 2007, 90, 9. 4078-4083. The detection is performed by a fluorometer after post-column reduction of menaquinone by Zn. Vitamin K1 is used as internal standard for extraction/purification steps and MK-4 (Sigma V9378) is used as external calibration for quantification.

The results are presented in Table 1, which shows the difference of production of menaquinone between the CNCM I-4128 and 23 other strains belonging to the *Lactococcus lactis* species (which were *Lactococcus lactis* subsp. *cremoris* or *Lactococcus lactis* subsp. *lactis* strains). Data are expressed in µgrams per 100 grams of freeze dried cells.

TABLE 1

| Strains | Total vitamin K2 expressed in µg/100 g of freeze dried cells |
|---|---|
| 1 | 78 |
| 2 | 49 |
| CNCM I-4128 | 267 |
| 3 | 91 |
| 4 | 48 |
| 5 | 60 |
| 6 | 59 |
| 7 | 79 |
| 8 | 62 |
| 9 | 94 |
| 10 | 42 |
| 11 | 68 |
| 12 | 38 |
| 13 | 12 |
| 14 | 57 |
| 15 | 73 |
| 16 | 68 |
| 17 | 79 |
| 18 | 28 |
| 19 | 36 |
| 20 | 130 |
| 21 | 73 |
| 22 | 63 |
| 23 | 94 |

Comparison of Production of Menaquinone (Vit. K2) for 24 Strains of *Lactococcus lactis*

The results of this experiment clearly show that the strain CNCM I-4128 has an outstanding ability to produce menaquinone compared to the 23 other strains tested.

Example 2: Measurement of the Production of Menaquinone by the Strain CNCM I-4128, Following TEST a The measure of the production of menaquinone by the strain CNCM I-4128 in the milk (following TEST A) has been repeated 11 times, according to the following protocol:
- inoculating two flasks comprising 100 mL of skimmed UHT milk, with $5.10^4$ to $10^7$ cfu/mL of the strain CNCM I-4128,
- incubating the inoculated flasks without stirring at a constant temperature selected in the range from 23° C. to 30° C. in a water bath,
- measuring and recording the evolution of the pH in one of the two flasks with a pH probe of a Cinac System (Ysebaert system),
- stopping the incubation when the pH reaches 4.60+/−0.1 by cooling down to 6° C. the flask wherein the pH has not been measured,
- storing said flask at 6° C. during 14 h to 20 h,
- homogenizing the milk manually.

The chemical extraction of menaquinone and the measurement of its quantity have then been performed according to the following protocol: 10 ml of milk obtained previously have been mixed with 5 ml of HCl 1N. The same protocol as in Example 1 has then been followed to perform the extraction of menaquinone and to measure its content.

Results are presented in table 2 hereinafter:

TABLE 2

| Experiment no | Total vitamin K2 expressed in µg/100 g of fermented milk |
|---|---|
| 1 | 7.3 |
| 2 | 9.9 |
| 3 | 12 |
| 4 | 12.3 |
| 5 | 15.2 |
| 6 | 9.8 |
| 7 | 12.2 |
| 8 | 12 |
| 9 | 16.3 |
| 10 | 8.7 |
| 11 | 11.6 |

Production of Vitamin K2 by CNCM I-4128 During Milk Maturation for Temperature Range Between 23° C. and 30° C., Results for 11 Independent Experiments These results show that the average production of CNCM I-4128 is 11.6 µg/100 g of fermented milk with a standard deviation of 2.5 µg/100 g.

Example 3: Measurement of the Production of Menaquinone by Strains CNCM 4128, DSM 23476, DSM 23477 and DSM 23478 by Test C

CNCM I-4128:

Freeze dried material has been produced according to test C and the menaquinone content in the freeze dried product has been evaluated thanks to protocol Q for extraction/purification and dosage.

TABLE A vitamin K2 concentration for CNCM-I-4128 - test C and protocol Q

| Sample | MK-6 ng/g | MK-7 ng/g | MK-8 ng/g | MK-9 ng/g | MK-10 ng/g | Total K2 µg/g | Average K2 µg/g of LYO | coefficient of variation |
|---|---|---|---|---|---|---|---|---|
| CNCM I-4128 | 1865 | 7443 | 48307 | 155025 | 4812 | 374 | 378.1 | 3.6% |
|  | 1736 | 6593 | 43810 | 156743 | 4061 | 367 |  |  |
|  | 2139 | 6912 | 57037 | 158733 | 4171 | 393 |  |  |

DSM 23476 and DSM 23477:

Freeze dried material has been produced according to test C and the menaquinone content in the freeze dried product has been evaluated thanks to protocol Q for extraction/purification and dosage.

TABLE B vitamin K2 concentration for DSM 23476 and DSM 23477 - test C and protocol Q - two trials test C+ protocol Q per strain

| Sample | MK-6 ng/g | MK-7 ng/g | MK-8 ng/g | MK-9 ng/g | Total K2 µg/g | Average K2 µg/g de LYO | coefficient of variation |
|---|---|---|---|---|---|---|---|
| DSM 23476 Trial no1 | 4026 | 5451 | 16842 | 24928 | 51.25 | 45.2 | 13.2% |
|  | 3623 | 4965 | 14361 | 16372 | 39.32 |  |  |
|  | 3698 | 5008 | 15866 | 20416 | 44.99 |  |  |
| DSM 23476 Trial no2 | 5104 | 7199 | 22166 | 30561 | 65.03 | 62.3 | 8.3% |
|  | 4860 | 6565 | 19144 | 25782 | 56.35 |  |  |
|  | 5649 | 8027 | 23437 | 28541 | 65.66 |  |  |

TABLE B-continued vitamin K2 concentration for DSM 23476 and DSM 23477 - test
C and protocol Q - two trials test C+ protocol Q per strain

| Sample | MK-6 ng/g | MK-7 ng/g | MK-8 ng/g | MK-9 ng/g | Total K2 µg/g | Average K2 µg/g de LYO | coefficient of variation |
|---|---|---|---|---|---|---|---|
| DSM 23477 | 1960 | 3980 | 13145 | 10208 | 29.30 | 28.4 | 4.0% |
| Trial no1 | 1795 | 3903 | 11518 | 9898 | 27.12 | | |
|  | 1690 | 3855 | 12719 | 10529 | 28.80 | | |
| DSM 23477 | 1422 | 3309 | 15970 | 18408 | 39.11 | 42.1 | 11.1% |
| Trial no2 | 1308 | 3176 | 16598 | 18554 | 39.64 | | |
|  | 1290 | 3093 | 19051 | 23975 | 47.41 | | |

DSM 23478:

Freeze dried material has been produced according to test C and the menaquinone content in the freeze dried product has been evaluated thanks to protocol Q for extraction/purification and dosage.

TABLE C vitamin K2 concentration for DSM 23478 -for different extractions/purification
step with the same freeze dried material obtained with Test C.

| Test | MK-4 ng/g | MK-5 ng/g | MK-6 ng/g | MK-7 ng/g | MK-8 ng/g | MK-9 ng/g | MK-10 ng/g | Total K2 µg/g | coefficient of variation |
|---|---|---|---|---|---|---|---|---|---|
| 1 | 135.8 | <100 | 178.7 | 1827.2 | 17597.1 | 60772.4 | 792.4 | 81.3 | 79.3 | 2.9% |
| 2 | 124.1 | <100 | 205.6 | 1935.2 | 18461.4 | 59126.8 | 695.7 | 80.5 | | |
| 3 | 204.2 | <100 | <100 | 1806.3 | 15680.9 | 57854.0 | 555.1 | 76.1 | | |
| 4 | 176.0 | <100 | 450.4 | 1941.5 | 16657.6 | 59727.2 | 618.8 | 79.6 | | |

Example 4: Measurement of the Production of Menaquinone by DSM 23479 by Test D

Strain DSM 23479 has been cultured as described in test D. Menaquinone production has then be measured according to protocol P. Results are presented in the table D hereinafter:

TABLE D

Production of Vitamin K2 by DSM 23479 - test D

| Test # | MK-4 ng/mL | MK-5 ng/mL | MK-6 ng/mL | MK-7 ng/mL | MK-8 ng/mL | MK-9 ng/mL | MK-10 ng/mL | K2 totale µg/100 mL (µg/100 g) |
|---|---|---|---|---|---|---|---|---|
| 1 | <1 | <1 | <1 | <1 | <1 | 3.8 | 261.4 | 26.5 |

The invention claimed is:

1. A method of enriching a milk product in menaquinone, wherein:

the method comprises:
  adding *Lactococcus lactis* subsp *cremoris* strain CNCM I-4128 or a *Lactococcus lactis* subsp *cremoris* variant thereof to a milk substrate,
  culturing the strain CNCM I-4128 or variant in the milk substrate, and
  obtaining a milk product enriched in menaquinone as compared to the milk substrate before the strain CNCM I-4128 or variant is added;
the strain CNCM I-4128 or variant:
  i) produces at least 12 µg of menaquinone per 100 g of milk fermented with the strain CNCM I-4128 or variant when measured by Test A, or
  ii) produces at least 260 µg of menaquinone per 100 g of freeze-dried cells when measured by Test B;
the strain CNCM I-4128 or variant is alive or under a frozen or freeze-dried preserved state when added to the milk substrate;

Test A comprises the following steps:
  inoculating two flasks comprising 100 mL of skimmed UHT milk, with $5 \times 10^4$ to $10^7$ cfu/mL of the strain to be tested,
  incubating the inoculated flasks without stirring at a constant temperature of from 23° C. to 30° C. in a water bath,
  measuring and recording the evolution of the pH in one of the two flasks with a pH probe,
  stopping the incubation when the pH reaches 4.60+/−0.1 by cooling to 6° C. the flask in which the pH has not been measured,
  storing the cooled flask at 6° C. for from 14 hours to 20 hours,
  manually homogenizing the milk, and
  performing a chemical extraction of menaquinone and measuring the quantity of menaquinone following Protocol P;
Test B comprises the following steps:
  culturing $1 \times 10^2$ to $1 \times 10^7$ cfu/ml of the strain to be tested for from 14 hours to 20 hours in 50 ml of M17-lactose broth medium at 30° C.,
  centrifuging 25 mL of the culture at 8000 rpm during 10 minutes, discarding the supernatant and resuspending the pellet with 25 mL of a tryptone salt solution containing 0.1% tryptone and 0.85% salt,
centrifuging the resuspended culture at 8000 rpm for 10 minutes,
discarding the supernatant and resuspending the pellet in 25 ml of reconstituted milk powder at 10% w/w,
placing the cell suspension in a freeze dryer,
obtaining from 2 to 4 g freeze-dried cells, and
performing a chemical extraction of menaquinone and measuring the quantity of menaquinone following Protocol P; and
Protocol P comprises the following steps:
preparing a sample in a tube, wherein:
when measuring the quantity of menaquinone from Test A, the sample consists of 10 mL of the fermented milk from Test A, and
when measuring the quantity of menaquinone from Test B, the sample consists of 10 mL of a 10 times dilution in ethanol/water, 50/50 V/V, of the freeze-dried cells from Test B,
mixing the sample with 5 ml of HCl 1N in the tube,
heating the resulting mixture in the tube at 100° C. for 10 min in a water bath,
adding 10 ml of isopranol to the tube,
placing the tube in a water bath equipped with ultrasound at 22° C. (+/−3° C.) for 10 minutes,
adding 5 ml of hexane to the tube,
mixing the contents of the tube by vortexing for 5 minutes,
centrifuging the resulting suspension at 4600 rpm for 5 minutes,
harvesting the organic phase,
centrifuging again for 5 min at 4600 rpm,
harvesting the organic phase,
concentrating the harvested organic phase with a speed vac system to obtain a dry product,
rehydrating the dry product with 1 ml ethanol,
filtrating the rehydrated product on a 0.45 µm filter to form an extract, and
injecting the extract into a high performance liquid chromatography (HPLC) system to separate and detect menaquinone, wherein:
the detection is performed using a fluorometer after post-column reduction of menaquinone by Zn,
vitamin K1 is used as an internal standard for the extraction/purification steps, and
menaquinone 4 (MK-4) is used as an external calibration for quantification.

2. The method of claim 1, wherein the variant produces at least 12 µg of menaquinone per 100 g of milk under Test A.

3. A method of preparing a fermented dairy product enriched in menaquinone, wherein:
the method comprises:
adding *Lactococcus lactis* subsp *cremoris* strain CNCM I-4128 or a *Lactococcus lactis* subsp *cremoris* variant thereof to a milk substrate,
fermenting the milk substrate inoculated with the strain CNCM I-4128 or variant, and
obtaining a fermented dairy product enriched in menaquinone as compared to the milk substrate before the strain CNCM I-4128 or variant is added to the milk substrate;
the strain CNCM I-4128 or variant:
i) produces at least 12 µg, of menaquinone per 100 g of milk fermented with the strain CNCM I-4128 or variant when measured by Test A, or
ii) produces at least 260 µg of menaquinone per 100 g of freeze-dried cells when measured by Test B;
the strain CNCM I-4128 or variant is alive or under a frozen or freeze-dried preserved state when added to the milk substrate;
Test A comprises the following steps:
inoculating two flasks comprising 100 mL of skimmed UHT milk, with $5 \times 10^4$ to $10^7$ cfu/mL of the strain to be tested,
incubating the inoculated flasks without stirring at a constant temperature of from 23° C. to 30° C. in a water bath,
measuring and recording the evolution of the pH in one of the two flasks with a pH probe,
stopping the incubation when the pH reaches 4.60+/−0.1 by cooling to 6° C. the flask in which the pH has not been measured,
storing the cooled flask at 6° C. for from 14 hours to 20 hours,
manually homogenizing the milk, and
performing a chemical extraction of menaquinone and measuring the quantity of menaquinone following Protocol P;
Test B comprises the following steps:
culturing $1 \times 10^2$ to $1 \times 10^7$ cfu/ml of the strain to be tested for from 14 hours to 20 hours in 50 ml of M17-lactose broth medium at 30° C.,
centrifuging 25 mL of the culture at 8000 rpm during 10 minutes,
discarding the supernatant and resuspending the pellet with 25 mL of a tryptone salt solution containing 0.1% tryptone and 0.85% salt,
centrifuging the resuspended culture at 8000 rpm for 10 minutes,
discarding the supernatant and resuspending the pellet in 25 ml of reconstituted milk powder at 10% w/w,
placing the cell suspension in a freeze dryer,
obtaining from 2 to 4 g freeze-dried cells, and
performing a chemical extraction of menaquinone and measuring the quantity of menaquinone following Protocol P; and
Protocol P comprises the following steps:
preparing a sample in a tube, wherein:
when measuring the quantity of menaquinone from Test A, the sample consists of 10 mL of the fermented milk from Test A, and
when measuring the quantity of menaquinone from Test B, the sample consists of 10 mL of a 10 times dilution in ethanol/water, 50/50 V/V, of the freeze-dried cells from Test B,
mixing the sample with 5 ml of HCl 1N in the tube,
heating the resulting mixture in the tube at 100° C. for 10 min in a water bath,
adding 10 ml of isopranol to the tube,
placing the tube in a water bath equipped with ultrasound at 22° C. (+/−3° C.) for 10 minutes,
adding 5 ml of hexane to the tube,
mixing the contents of the tube by vortexing for 5 minutes,
centrifuging the resulting suspension at 4600 rpm for 5 minutes,
harvesting the organic phase,
centrifuging again for 5 min at 4600 rpm,
harvesting the organic phase,
concentrating the harvested organic phase with a speed vac system to obtain a dry product,
rehydrating the dry product with 1 ml ethanol, filtrating the rehydrated product on a 0.45 µm filter to form an extract, and injecting the extract into a high performance liquid chromatography (HPLC) system to separate and detect menaquinone, wherein:

the detection is performed using a fluorometer after post-column reduction of menaquinone by Zn, vitamin K1 is used as an internal standard for the extraction/purification steps, and menaquinone 4 (MK-4) is used as an external calibration for quantification.

4. The method of claim 3, wherein the milk substrate is selected from the group consisting of natural milk, reconstituted milk, skimmed milk, milk-based media and media based on products of dairy origin.

5. The method of claim 3, wherein the dairy product is selected from the group consisting of a fermented milk, a yogurt, a matured cream, a cheese, a milk drink, a dairy product retentate, a processed cheese, a cream dessert, a cottage cheese and an infant milk.

6. The method of claim 3, wherein the variant produces at least 12 µg of menaquinone per 100 g of milk under Test A.

7. The method of claim 1, wherein the method comprises adding the strain CNCM I-4128 to the milk substrate.

8. The method of claim 7, wherein the strain CNCM I-4128 is in an alive non-preserved state at the time the strain CNCM I-4128 is added to the milk substrate.

9. The method of claim 7, wherein the strain CNCM I-4128 is under a frozen or freeze-dried preserved state at the time the strain CNCM I-4128 is added to the milk substrate.

10. The method of claim 1, wherein the strain CNCM I-4128 or variant is in an alive non-preserved state at the time the strain CNCM I-4128 or variant is added to the milk substrate.

11. The method of claim 1, wherein the strain CNCM I-4128 or variant is under a frozen or freeze-dried preserved state at the time the strain CNCM I-4128 or variant is added to the milk substrate.

12. The method of claim 1, wherein the variant produces at least 260 µg of menaquinone per 100 g of freeze-dried cells under Test B.

13. The method of claim 2, wherein the variant produces at least 260 µg of menaquinone per 100 g of freeze-dried cells under Test B.

14. The method of claim 3, wherein the method comprises culturing the strain CNCM I-4128 in the milk substrate.

15. The method of claim 14, wherein the strain CNCM I-4128 is in an alive non-preserved state at the time the strain CNCM I-4128 is added to the milk substrate.

16. The method of claim 14, wherein the strain CNCM I-4128 is under a frozen or freeze-dried preserved state at the time the strain CNCM I-4128 is added to the milk substrate.

17. The method of claim 3, wherein the strain CNCM I-4128 or variant is in an alive non-preserved state at the time the strain CNCM I-4128 or variant is added to the milk substrate.

18. The method of claim 3, wherein the strain CNCM I-4128 or variant is under a frozen or freeze-dried preserved state at the time the strain CNCM I-4128 or variant is added to the milk substrate.

19. The method of claim 3, wherein the variant produces at least 260 µg of menaquinone per 100 g of freeze-dried cells under Test B.

20. The method of claim 6, wherein the variant produces at least 260 µg of menaquinone per 100 g of freeze-dried cells under Test B.

* * * * *